United States Patent [19]

Hays et al.

[11] Patent Number: 5,068,196
[45] Date of Patent: Nov. 26, 1991

[54] METHOD FOR DETERMINING FLUID CORROSIVENESS

[75] Inventors: George F. Hays, Morristown; James A. Coyle, Booton, both of N.J.

[73] Assignee: Ashland Oil Inc., Russell, Ky.

[21] Appl. No.: 485,588

[22] Filed: Feb. 27, 1990

Related U.S. Application Data

[62] Division of Ser. No. 813,727, Dec. 27, 1985, abandoned.

[51] Int. Cl.⁵ .................................................. G01N 17/00
[52] U.S. Cl. .................................... 436/6; 73/61.2; 422/53; 436/147; 436/149; 436/151
[58] Field of Search ............... 436/6, 147, 149, 151; 422/53; 73/61.2

[56] References Cited

U.S. PATENT DOCUMENTS 3,108,468 10/1963 Mickel .
3,627,493 12/1971 Manley ............................ 422/53
4,138,878 2/1979 Holmes et al. ................. 73/61.2 X
4,339,945 7/1982 Knudsen et al. ............... 422/53 X

*Primary Examiner*—Jill Johnston
*Attorney, Agent, or Firm*—Louis E. Marn

[57] ABSTRACT

There is disclosed a portable apparatus and process for using same including a test conduit assembly and related conduit valve and fluid flow assemblies for conecting to a process unit for fluid flow communication with the test conduit assembly for passing a fluid to be evaluated for corrosive effect on such test conduit assembly wherein the test conduit assembly includes a test conduit of a predetermined length disposed in a transparent conduit section for passing the fluid therethrough and wherein a heating unit of a predetermined length is disposed in the test conduit wherein the heating unit is of a length of at least about 2 inches and comprises less than about 50 percent of the predetermined length of the test conduit.

1 Claim, 1 Drawing Sheet

METHOD FOR DETERMINING FLUID CORROSIVENESS

This is a division of application Ser. No. 06/813,372, filed Dec. 27, 1985.

BACKGROUND OF THE INVENTION

1) Field of the Invention

This invention relates to a process and apparatus for testing fluids, and more particularly to an improved process and apparatus for testing the corrosion effects of a fluid to a metallic surface.

2) Description of the Prior Art

The chemical water treatment industry has historically been involved with reducing or inhibiting the inherent scale forming or fouling tendencies of natural waters associated with large industrial cooling water systems. Many of the foulant components found in water systems originate with the incoming supply, but some contaminants enter the system from the local environment or from process contamination.

In U.S. Pat. No. 4,339,945, assigned to the same assignee as the instant application, there is disclosed a novel mobile apparatus and process therefor including a heat transfer test assembly and related conduit and valve assemblies for connection in fluid flow communication to a heat transfer apparatus for in situ testing of the fluid passing therethrough and including monitoring and recording apparatus. The heat transfer test assembly includes a heating member for controlled heat input and thermocouples to measure the wall temperature of the heating member to permit fouling determinations at varying flow rates with simultaneous monitoring and recording thereof together with data, such as corrosion, pH, conductivity, and the like. The mobile unit is difficult to conveniently move from one location to another and provides data with respect to the corrosion effect of a test fluid in a heat transfer environment. Additionally, the heating member includes a resistant heating element embedded therein and consequently such heating member is discarded after use.

In U.S. application Ser. No. 274,880, filed June 18, 1981, assigned to the same assignee as the instant application, there is disclosed a fouling and corrosion test assembly comprised of a metallic tube having a heating element embedded in a heat conductive material for controlled heat input and with a thermocouple to measure wall temperature of the tube, and a metallic sleeve disposed about a predetermined portion of the metallic tube. The fouling and corrosion test assembly is disposed within a conduit including valve assemblies to be placed for a predetermined time period in fluid flow communication with a fluid to determine corrosion rate, etc. by weight loss of the metallic sleeve under controlled heat input, temperature conditions and fluid flow rates. All such prior methods and apparatus related to corrosion and fouling as related to heat transfer conditions. There exists a need to evaluate corrosion and fouling of a fluid to a surface in heat transfer and non-heat transfer relationships to provide corrosion and folding data and thereby to provide for more effective design factors of heat transfer assemblies.

OBJECTS OF THE INVENTION

An object of the present invention is to provide a portable process and apparatus for in situ testing of a fluid on heat transfer and non-heat transfer surfaces to determine corrosion effects thereon.

Another object of the present invention is to provide a portable process and apparatus for in situ testing of a fluid on heat transfer and non-heat transfer surfaces to determine corrosion effects thereon permitting facile recording of data for subsequent data correlation.

Yet another object of the present invention is to provide a portable process and apparatus for in situ testing of a fluid on heat transfer and non-heat transfer surfaces to determine corrosion effects thereon which is readily assembled and dismantled to provide corrosion data.

Still another object of the present invention is to provide a portable process and apparatus for in situ testing of a fluid on heat transfer and non-heat transfer surfaces to determine corrosion effects thereon as well as fouling as a result of biological activity.

A still further object of the present invention is to provide a portable process and apparatus for in situ testing of a fluid on heat transfer and non-heat transfer surfaces to determine corrosion effects thereon as well as severity of fouling.

Another object of the present invention is to provide a portable process and apparatus for in situ testing of a fluid on heat transfer and non-heat transfer surfaces to determine corrosion effects thereon as well as fouling as a result of scale formation.

SUMMARY OF THE INVENTION

These and other objects of the present invention are achieved by a portable apparatus and process for using same including a test conduit assembly and related conduit valve and fluid flow assemblies for connecting to a process unit for fluid flow communication with the test conduit assembly for passing a fluid to be evaluated for corrosive effect on such test conduit assembly wherein the test conduit assembly includes a test conduit of a predetermined length disposed in a transparent conduit section for passing the fluid therethrough and wherein a heating unit of a predetermined length is disposed in the test conduit wherein the heating unit is of a length of at least about 2 inches and comprises less than about 50 percent of the predetermined length of the test conduit.

BRIEF DESCRIPTION OF THE DRAWINGS

Further objects and advantages of the present invention will become apparent upon consideration of the detailed disclosure thereof, especially when taken with the accompanying drawings wherein like numerals designate like parts throughout and wherein.

DETAILED DESCRIPTION OF THE DRAWINGS

Figure 1:
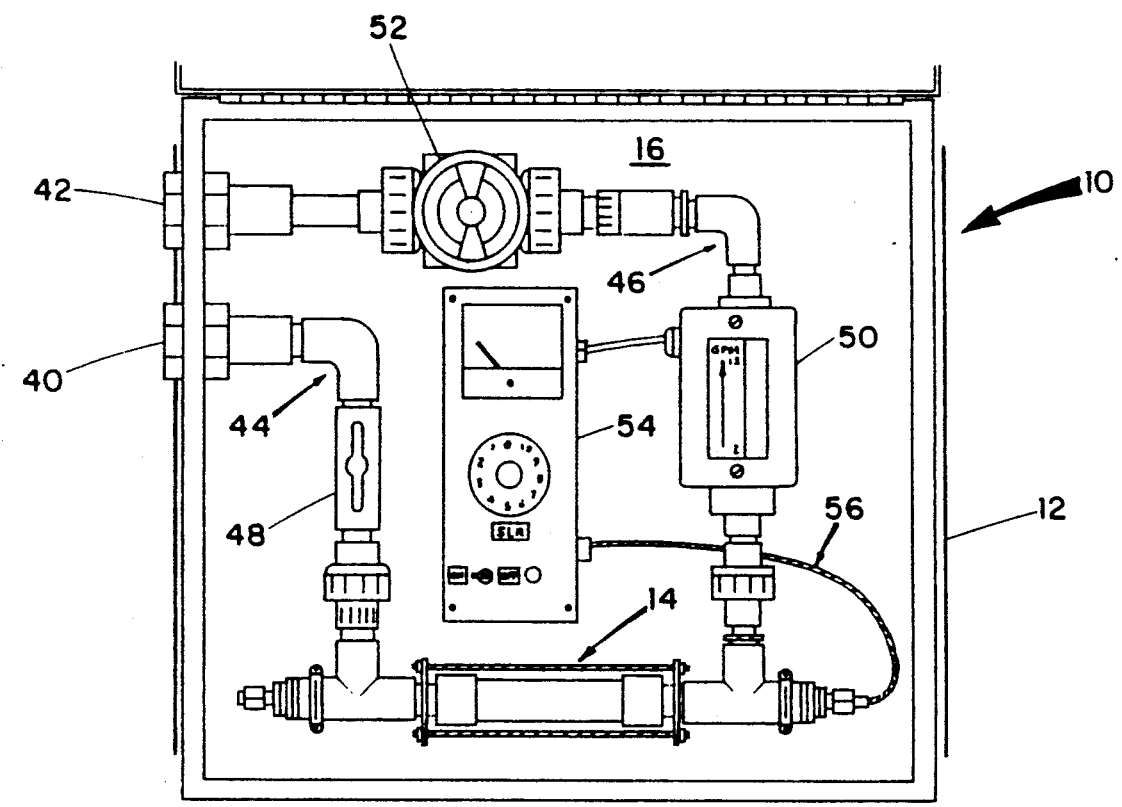
FIG. 1 is an elevational view of the portable apparatus of the present invention.

Referring now to the drawings, and particularly to FIG. 1, there is illustrated a corrosion test assembly, generally indicated as 10, comprised of a housing 12 in which is disposed a test unit, generally indicated as 14, and related conduit and fluid flow control, generally indicated as 16.

Figure 2:
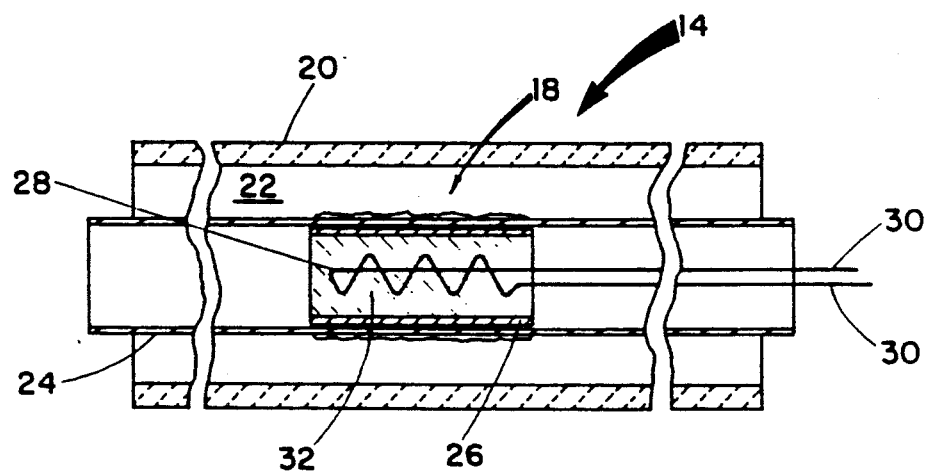
FIG. 2 is an enlarged, somewhat schematic cross-sectional view of the test conduit assembly.

The test unit 14, referring more specifically to FIG. 2, is comprised of a test conduit assembly, generally indicated as 18, coaxially disposed within a conduit 20 forming an annular passageway 22. The test conduit assembly 18 is comprised of a predetermined length of a test conduit member 24 in which is disposed a cylindrically-shaped cartridge member 26 including a high resistant heating element 28 including conductors 30 embedded within an insulting matrix 32, such as magnesium oxide. The cartridge member 26 is formed to provide for close fitting contact within the test conduit member 24 to ensure good heat transfer across the contacting surfaces as well as to prevent overheating and burn-out of the cartridge member 26, i.e. the outer diameter of the cartridge member 26 is slightly smaller than the inner diameter of the test conduit member 24 to permit facile assembly of the former within the latter.

The test conduit member 24 is formed of a metallic material, such as stainless steel, copper, titanium, mild steel, admiralty metal or the like, dependent, for example, on the tube material of a heat exchanger being evaluated or to be designed for the fluid to be tested by passage through the test unit 14, or of like metallic material to that in the unit through which the fluid to be tested is flowing. Generally, mild steel or stainless steel is used for normal cooling water application, whereas admiralty brass is employed for sea water and brackish water applications. The conduit 20 is preferably formed of any suitable transparent material, such as glass, to permit visual observation of fluid flow as well as any scale formation about the surface of the test conduit member 24.

The cartridge member 26 is of a length sufficient to provide a steady state of heat transfer at any desired energy level, however, is less than about fifty percent (50%) of the length of the test conduit member 24. In such dimensional relationship, the corrosion and fouling effect of the fluid on the test conduit member 24 may be measured with respect to a heat transfer and a non-heat transfer relationship, as more fully hereinafter discussed.

The test conduit assembly 14 is disposed within the conduit and fluid flow control 16 within the housing 12. Referring again to FIG. 1, the conduit and fluid flow control 16 includes inlet and outlet couplings 40 and 42 for connection to a process unit (not shown). The couplings 40 and 42 are connected in fluid flow relationship to the test conduit member 24 by an inlet conduit assembly and an outlet conduit assembly, generally indicated as 44 and 46, respectively. The inlet conduit assembly 44 includes a shut-off valve 48. The outlet conduit assembly 46 includes a fluid flow measuring device 50 and a valve 52 for controlling the rate of fluid flow through the test conduit assembly 14. The fluid flow measuring device may also function as a low flow cut-off. The conduit 20 permits visual observation of corrosion, fouling and scale build-up about the test conduit member 24. The portable test assembly 10 is provided with a power controller device 54 having voltage settings from 0 to 220 YAC including conductors 56 for connection to the conductors 30 of the heating element of the heating cartridge 26.

In operation, a test conduit 24 of a predetermined length and preselect metallurgy is cleaned and weighed. The heating cartridge 26 is inserted into the test conduit 24, and is preferably coated with a heat transfer paste to assist in close fitting of the heating cartridge 26 therein as well as to assist in the heat transfer relationship. The test conduit assembly 18 is then inserted within the conduit 20 and coupled to the inlet and outlet conduit assemblies 44 and 46. Thereafter, a conduit (not shown) from a process unit (not shown) containing a fluid to be tested is connected to the inlet coupling 40 and a conduit (not shown) is coupled to the outlet coupling 42 for return to the process unit. Fluid flow through the test assembly 10 is controlled by valve 52 whereas power to the heating cartridge 26 is controlled by adjusting the power controller 54 at diverse power inputs. It is understood that a pump or other means may be provided to assist in effecting fluid flow through the assembly 10 including fluid flow about the test conduit member 24 during test protocol during which flow data, power data, etc. are recorded and visual inspection periodically made and data recorded of the test conduit member 24.

After a predetermined time, the test protocol is discontinued and the test conduit member 24 is removed from the test conduit assembly. The test conduit member 24 is cleaned with the deposits analyzed. Thereafter, the test conduit member 24 is severed into a part constituting the heat transfer portion and parts constituting the non-heat transfer portions, and unexposed parts with the parts measured, weighed and compared to original weight to provide results as to corrosion, fouling, etc. as selected to heat and non-heat transfer surfaces as correlated against rates of fluid flow and power input.

While the present invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

what is claimed:

1. A method for determining corrosiveness of a fluid, which comprises:

weighing a metallic test conduit member of a predetermined length and having a channel therethrough;

positioning a cylindrically-shaped heating cartridge of a predetermined length in close fitting relationship within said channel of said metallic test conduit member, said predetermined length of said cylindrically-shaped cartridge being less than said predetermined length of said metallic test conduit member thereby defining a heat transfer surface and a non-heat transfer surface about said metallic test conduit member;

positioning said metallic test conduit member within a conduit member thereby defining a fluid flow passageway therebetween;

passing said fluid through said fluid flow passageway for a preselect time period;

energizing said heating carriage during said preselect time period;

recording rate of fluid flow and power to said heating cartridge;

removing said metallic test conduit member form within said conduit member;

removing said hating cartridge from said metallic test conduit member;

dissecting said metallic test conduit member into a portion of said heat transfer surface and a portion of said non-heat transfer surface; and weighing said potions to provide data for evaluating with said fluid flow rate and power input of corrosion so did fluid to said heat transfer surface and said non-heat transfer surface of said metallic test conduit.

* * * * *